(12) United States Patent
Chen et al.

(10) Patent No.: US 10,929,991 B2
(45) Date of Patent: Feb. 23, 2021

(54) SYSTEM AND METHOD FOR CREATING REGISTERED IMAGES

(71) Applicant: MacKay Memorial Hospital, Taipei (TW)

(72) Inventors: Yu-Jen Chen, Taipei (TW); Kai-Lung Hua, Taipei (TW); Hung-Chi Tai, Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 72 days.

(21) Appl. No.: 16/517,549

(22) Filed: Jul. 20, 2019

(65) Prior Publication Data

US 2020/0027264 A1 Jan. 23, 2020

Related U.S. Application Data

(60) Provisional application No. 62/700,920, filed on Jul. 20, 2018.

(51) Int. Cl.
| | |
|---|---|
| *G06T 7/33* | (2017.01) |
| *G06T 17/00* | (2006.01) |
| *A61N 5/10* | (2006.01) |
| *G16H 30/40* | (2018.01) |
| *G16H 50/20* | (2018.01) |
| *G16H 20/40* | (2018.01) |
| *G16H 50/50* | (2018.01) |
| *G06T 7/38* | (2017.01) |
| *G06T 7/149* | (2017.01) |

(52) U.S. Cl.
CPC ............... *G06T 7/38* (2017.01); *A61N 5/103* (2013.01); *A61N 5/1039* (2013.01); *G06T 7/149* (2017.01); *G06T 7/33* (2017.01); *G06T 17/00* (2013.01); *G16H 20/40* (2018.01); *G16H 30/40* (2018.01); *G16H 50/20* (2018.01); *G16H 50/50* (2018.01); *G06T 2207/10081* (2013.01); *G06T 2207/10084* (2013.01); *G06T 2207/20116* (2013.01); *G06T 2210/32* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 2007/0043286 A1* | 2/2007 | Lu | A61N 5/1048 600/407 |
| 2019/0295268 A1* | 9/2019 | Gass | G06T 5/004 |
| 2020/0279414 A1* | 9/2020 | Andersson | G06F 16/53 |

\* cited by examiner

*Primary Examiner* — Justin P. Misleh

(57) ABSTRACT

Disclosed herein are a method and a system for creating a registered image that integrates the information of CT and CBCT images. With the present method and system, medical practitioners can precisely transform the information of CT image-based treatment plan into the CBCT image so as to accurately control the dosage and location of a radiation therapy. Accordingly, also disclosed herein are methods of treating a cancer in the subject with the aid of the method and/or system of the present disclosure.

17 Claims, 4 Drawing Sheets
(1 of 4 Drawing Sheet(s) Filed in Color)

200

(A)  (B)

SYSTEM AND METHOD FOR CREATING REGISTERED IMAGES

CROSS-REFERENCE TO RELATED APPLICATIONS

This application claims priority to U.S. Provisional Patent Application No. 62/700,920, filed Jul. 20, 2018, which is incorporated herein by reference in its entirety.

BACKGROUND OF THE INVENTION

1. Field of the Invention

The present disclosure in general relates to the field of biological imaging, particularly to medical imaging. More specifically, the present disclosure relates to a system and a method for registering images obtained from computed tomography (CT) scan and cone-beam computed tomography (CBCT) scan; and their clinical uses in radiotherapy.

2. Description of Related Art

CT scan, also called X-ray computed tomography (X-ray CT) or computerized axial tomography scan (CAT scan), makes use of computer-processed combinations of X-ray images taken at various angles to produce cross-sectional (tomographic) images of specific areas of a scanned object, allowing one (e.g., a physician) to view the interior of the object without cutting it open. Compared with traditional 2D medical radiography, CT scan possesses the advantages of, (1) eliminating the superimposed images of structures outside the area of interest; (2) distinguishing tissues with respective physical densities differing by less than 1%; and (3) producing multiplanar reformatted images.

Cone beam computed tomography (or CBCT, also referred to as C-arm CT, cone beam volume CT, or flat panel CT) is a medical imaging technique consisting of X-ray computed tomography where the X-rays are divergent, forming a cone. CBCT provides adequate image quality at a lower exposure dose. Compared with CT, CBCT has the advantages of being low cost, short scanning time, and less image artifacts.

In clinical treatment, radiotherapy execution usually includes two stages: (1) designing a radiotherapy plan (also known as radiation therapy plan) based on the CT dataset; and (2) locating the precise treatment areas in accordance with the CBCT dataset. Specifically, the radiotherapy plan is the process, in which a team consisting of radiation oncologists, radiation therapist, medical physicists and medical dosimetrists plan the appropriate external beam radiation therapy and/or internal radiation therapy (i.e., brachytherapy) for a cancer patient. Typically, the medical images derived from CT scan are used to form a virtual patient for a computer-aided design procedure. Treatment simulations are performed to plan the geometric, radiological, and dosimetric aspects of the therapy. Further, since CBCT provides volumetric imaging for radiographic monitoring throughout the treatment process, a CBCT image is obtained before each treatment so as to promptly and precisely locate the tumors and the surrounding tissues. However, in actual practice, the transformation between the planning CT and CBCT images is oftentimes associated with deformations, which results in shifting of the locations of tumor and its surrounding organs.

In view of the foregoing, there exists in the related art a need for an improved system and method for precisely transforming the CT images into the CBCT images so as to generate the real-time treatment information comprising the treatment plan and the CBCT image data.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a system for creating a registered image from a plurality of CT images and a plurality of CBCT images. The present system comprises a user interface, which is configured to receive an input of commands from a user and provide an output to the user; and a processing unit, which is controlled by the user interface and is configured to, (a) respectively contour the plurality of CT images and the plurality of CBCT images to create a plurality of contoured CT images and a plurality of contoured CBCT images;

(b) respectively extract the plurality of contoured CT images and the plurality of contoured CBCT images of the step (a) to create a plurality of extracted CT images and a plurality of extracted CBCT images;

(c) respectively construct a three dimensional (3D) CT model and a 3D CBCT model from the plurality of extracted CT images and the plurality of extracted CBCT images of the step (b);

(d) create a registered 3D CBCT model by matching the 3D CBCT model to the 3D CT model of the step (c);

(e) respectively generate a plurality of transverse CT images and a plurality of transverse CBCT images from the 3D CT model of the step (c) and the registered 3D CBCT model of the step (d);

(f) respectively select one target transverse CT image and one target transverse CBCT image from the plurality of transverse CT images and the plurality of transverse CBCT images of the step (e); and (g) register the respectively selected target transverse CT image and CBCT image of the step (f) to create the registered image.

According to certain embodiments of the present disclosure, in the step (b), the plurality of contoured CT images and the plurality of contoured CBCT images are respectively extracted by equation (i), $$F_1(C)+F_2(C)=\int_{inside(C)}|u_0-c_1|^2 dx + \int_{outside(C)}|u_0-c_2|^2 dx \quad (i),$$

wherein, in the creation of each of the plurality of extracted CT images, C is the contoured CT image, $c_1$ is the average value of pixel intensity inside the contoured CT image, $c_2$ is the average value of pixel intensity outside the contoured CT image, $u_0$ is the CT image; and x is the coordinate of the CT image; and in the creation of each of the plurality of extracted CBCT images, C is the contoured CBCT image, $c_1$ is the average value of pixel intensity inside the contoured CBCT image, $c_2$ is the average value of pixel intensity outside the contoured CBCT image, $u_0$ is the CBCT image; and x is the coordinate of the CBCT image.

According to some embodiments of the present disclosure, in the step (d), the registered 3D CBCT model is created by equation (ii), $$E = \sum_{i=1}^{N} \left| (\vec{p_i'} - \overline{p_i}) - [R(\vec{q_i'} - \overline{q_i}) + T] \right|, \quad (ii)$$

wherein, $\vec{p}$ is the grid origin coordinate of the 3D CBCT model, $\vec{p_i}$ is the number i point of the 3D CBCT model, $\vec{p_i'}$ is $\vec{p_i} - \vec{p}$, $\vec{q}$ is the grid origin coordinate of the 3D CT model, $\vec{q_i}$ is the number i point of the 3D CBCT model, $\vec{q_i'}$ is $\vec{q_i} - \vec{q}$, T is a translation vector, and R is a rotation matrix to minimize the value of error E.

According to some embodiments of the present disclosure, in the step (f), the target transverse CT image and the target transverse CBCT image are selected by equation (iii), $$\sum_{x',y'} [I(x', y') - I(x - x', y - y')]^2, \quad (iii)$$

wherein, x and y are the coordinates of each of the plurality of transverse CT image, x' and y' are the coordinates of each of the plurality of transverse CBCT image, and I is a number to minimize the value of equation (iii).

According to certain embodiments of the present disclosure, in the step (g), the respectively selected target transverse CT image and CBCT image of step (f) are registered by equation (iv), $$dr^{(k+1)} = \frac{(I_m^{(k)} - I_s)\nabla I_s}{\left(I_m^{(k)} - I_s\right)^2 + |\nabla I_s|^2} + \frac{(I_m^{(k)} - I_s)\nabla I_m^{(k)}}{\left(I_m^{(k)} - I_s\right)^2 + |\nabla I_m^{(k)}|^2}, \quad (iv)$$

wherein, dr is the voxels of the target transverse CT image and the target transverse CBCT image, $I_m^{(k)}$ is the intensity of the target transverse CT image at the kth iteration, and Is is the target transverse CBCT image.

Optionally, the system may further comprise a communication port that is coupled to the user interface. According to some embodiments of the present disclosure, the communication port is a serial port, universal serial bus (USB) port, or micro-USB port.

According to certain embodiments of the present disclosure, the processing unit is further configured to respectively convert the plurality of CT images and the plurality of CBCT images from a first file format into a second file format. In one working example, the first file format is digital imaging and communications in medicine (DICOM) format, and the second file format is tagged image file format (TIFF) or joint photographic expert group (JPEG) format. According to the example, the conversion is exerted by MATrix LABoratory (MATLAB) program.

Another aspect of the present disclosure pertains to a computer implemented method for creating a registered image from a plurality of CT images and a plurality of CBCT images. The computer implemented method comprises the steps of, (a) respectively contouring the plurality of CT images and the plurality of CBCT images to create a plurality of contoured CT images and a plurality of contoured CBCT images;

(b) respectively extracting the plurality of contoured CT images and the plurality of contoured CBCT images of the step (a) to create a plurality of extracted CT images and a plurality of extracted CBCT images;

(c) respectively constructing a 3D CT model and a 3D CBCT model from the plurality of extracted CT images and the plurality of extracted CBCT images of the step (b);

(d) creating a registered 3D CBCT model by matching the 3D CBCT model to the 3D CT model of the step (c);

(e) respectively generating a plurality of transverse CT images and a plurality of transverse CBCT images from the 3D CT model of the step (c) and the registered 3D CBCT model of the step (d);

(f) respectively selecting one target transverse CT image and one target transverse CBCT image from the plurality of transverse CT images and the plurality of transverse CBCT images of the step (e); and (g) registering the respectively selected target transverse CT image and CBCT image of the step (f) to create the registered image.

The computer implemented method for creating the registered image is quite similar to the method executed by the present system as described above, and hence, detailed description thereof is omitted herein for the sake of brevity.

According to some embodiments of the present disclosure, for the purpose of creating a registered image with treatment plant, the computer implemented method further comprises a step of generating a treatment plan on the plurality of CT images prior to step (a), and thus, one person skilled in the art or a practitioner accordingly may administer to a subject in need thereof an appropriate treatment (e.g., radiation therapy) in accordance with the treatment plan of the registered image.

Also disclosed herein is a method of treating a cancer in the subject. The method comprises, (a) obtaining a plurality of CT images and a plurality of CBCT images of the subject;

(b) generating a treatment plan on the plurality of CT images of the step (a);

(c) creating a registered image with the treatment plan from the plurality of CT images of the step (b) and the plurality of CBCT images of the step (a) by the computer implemented method of the present disclosure; and (d) administering to the subject a treatment in accordance with the registered image of the step (c).

According to some embodiments, the treatment is a radiotherapy.

The cancer treatable with the present system and/or method may be a melanoma, leukemia, brain tumor, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, cervical cancer, ovarian cancer, prostate cancer, or head and neck squamous cell carcinoma.

The subject is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

Figure 1:
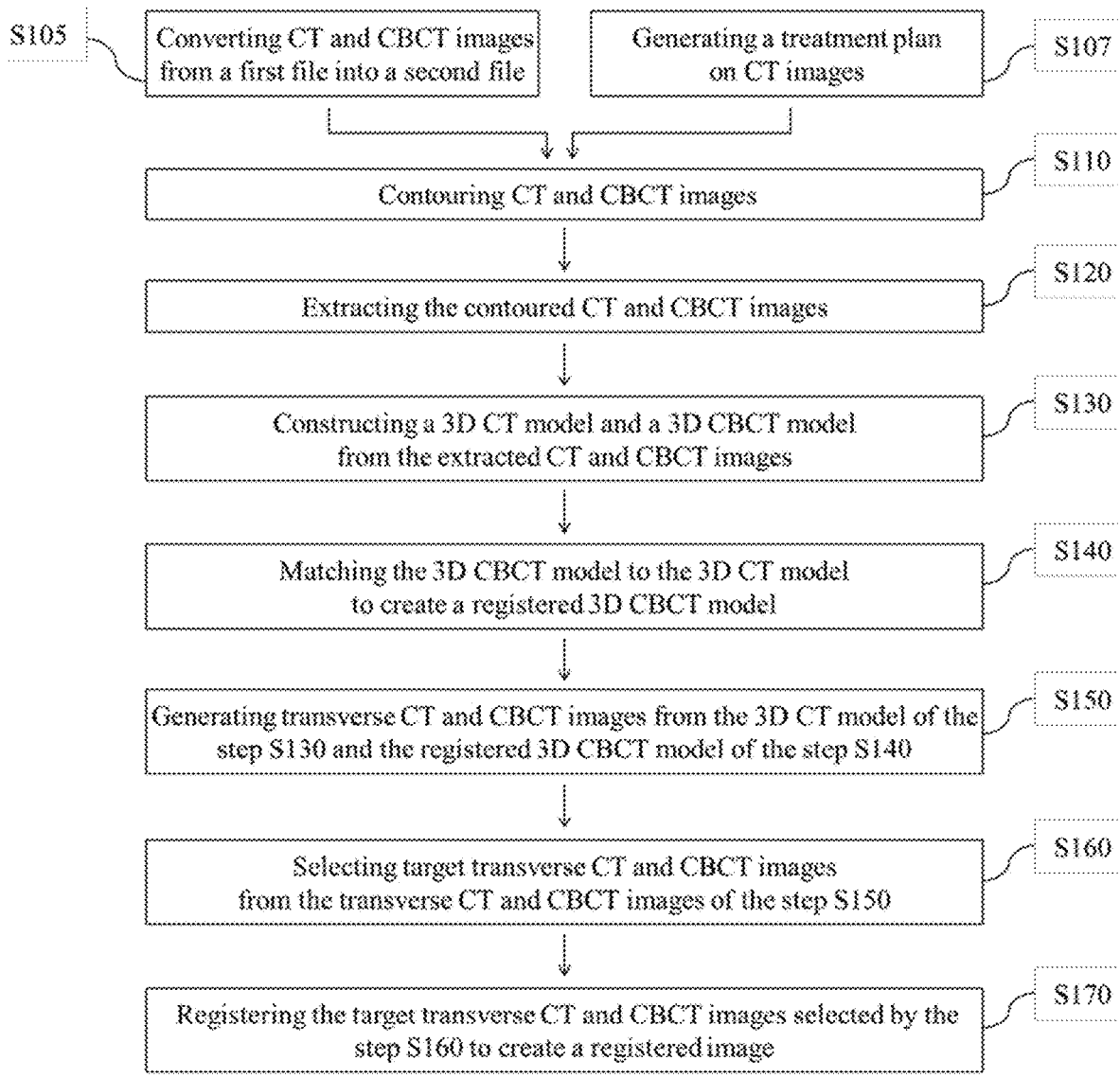
FIG. 1 is a flow chart illustrating a method 100 according to one embodiment of the present disclosure.
Figure 2:
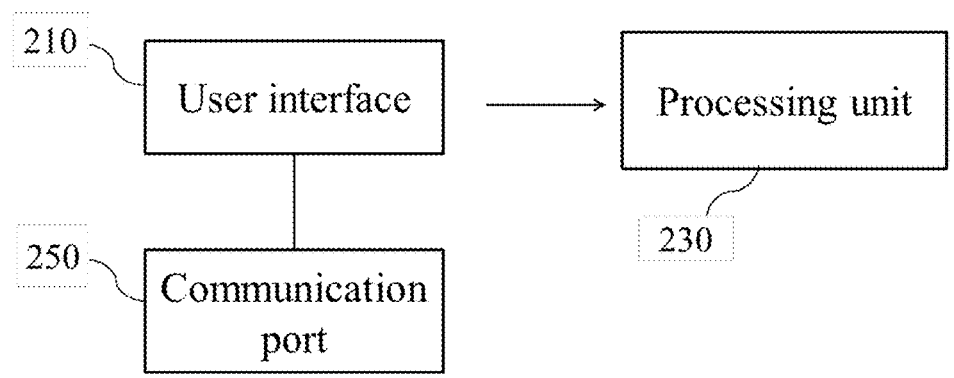
FIG. 2 is a schematic diagram illustrating a system 200 according to another embodiment of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

An image (e.g., a CT or CBCT image) is considered to be "in register" with another image (e.g., a CBCT or CT image) that is in the field of view when the two images are visually aligned from the perspective of the observer. As the term "registered" is used in the present disclosure, a registered feature of one image (e.g., a CT or CBCT image) is sized, positioned, and oriented on the display so that its appearance represents the size, position, and orientation of the corresponding image (e.g., a CBCT or CT image), correlated to the field of view of the observer. Registration may be in two dimensions (2D) or three dimensions (3D) in accordance with desired purposes. The term "registered image" refers to a sample image (e.g., a CT or CBCT image) that has been registered in relation to the reference image (e.g., a CBCT or CT image) to form or provide the registered image.

The term "transverse" refers to a direction substantially perpendicular to the plane of the longitudinal and lateral directions. Directions within ±45 degrees of the transverse direction are considered to be "transverse."

The term "treatment" or "treating" as used herein is intended to mean obtaining a desired pharmacological and/or physiologic effect, e.g., inhibiting cancer growth. The effect may be prophylactic in terms of completely or partially preventing a disease or symptom thereof and/or therapeutic in terms of a partial or complete cure for a disease and/or adverse effect attributable to the disease. The term "treatment" or "treating" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "subject" refers to a mammal including the human species that is treatable with the system and/or methods of the present invention. The term "subject" is intended to refer to both the male and female gender unless one ge'nder is specifically indicated.

The terms "tumor," "cancer" and "carcinoma as used herein are interchangeable and intended to mean any cellular malignancy whose unique trait is the loss of normal controls that results in unregulated growth, lack of differentiation and ability to invade local tissues and metastasize. Tumor can develop in any organ or tissue, and may be any of melanoma, leukemia, brain tumor, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, cervical cancer, ovarian cancer, prostate cancer, or head and neck squamous cell carcinoma.

Radiotherapy (also known as radiation therapy, or radiation treatment) is a treatment involving the use of high-energy radiation to control or kill malignant cells. Since the high-energy radiation would damage the DNA of cells and lead to the cellular death, an appropriate treatment plan is needed to treat the tumor without damaging the normal tissues (such as, skin or organs surrounding the tumor). Clinically, a CT image is usually acquired prior to the radiotherapy; the clinical practitioners can then design a treatment plan based on the CT images to optimize the radiotherapy. On the other hand, as the tumor grows exponentially and might be accompanied with metastasis, the CBCT scan is taken before each treatment so as to accurately localize the tumors and their surrounding tissues. To efficiently integrate the information of the two systems, the present invention aims at providing a method and a system for registering an image derived from CT scan and CBCT scan. Accordingly, the clinical practitioners can accurately perform the radiotherapy in light of the registered image.

I. Method for Creating an Registered Image from CT Scan and CBCT Scan

The first aspect of the present disclosure is directed to a method for creating a registered image from a plurality of CT images and a plurality of CBCT images. Reference is made to FIG. 1, which is a flow chart of a method 100 implemented on a computer according to embodiments of the present disclosure. The method 100 comprises the steps of, (S110) respectively contouring the plurality of CT images and the plurality of CBCT images to create a plurality of contoured CT images and a plurality of contoured CBCT images;

(S120) respectively extracting the plurality of contoured CT images and the plurality of contoured CBCT images of the step S110 to create a plurality of extracted CT images and a plurality of extracted CBCT images;

(S130) respectively constructing a 3D CT model and a 3D CBCT model from the plurality of extracted CT images and the plurality of extracted CBCT images of the step S120;

(S140) creating a registered 3D CBCT model by matching the 3D CBCT model to the 3D CT model of the step S130;

(S150) respectively generating a plurality of transverse CT images and a plurality of transverse CBCT images from the 3D CT model of the step S130 and the registered 3D CBCT model of the step S140;

(S160) respectively selecting one target transverse CT image and one target transverse CBCT image from the plurality of transverse CT images and the plurality of transverse CBCT images of the step S150; and (S170) registering the respectively selected target transverse CT image and CBCT image of the step S160 to create the registered image.

Before the method 100 is implemented, a subject is first subjected to a CT scan and a CBCT scan so that CT and CBCT images of the region of interest may be respectively derived therefrom. The region of interest may be a region within brain, neck, spine, chest, abdomen, pelvis, or sinuses, depending on the symptom and/or condition of the subject underwent CT and CBCT scans. In one working example, the region of interest is within the brain, and accordingly, brain CT and CBCT images are respectively obtained from the CT and CBCT scans.

Optionally, prior to the step S110, the method 100 may further comprise a step S105 of converting each of the CT and CBCT images (e.g., brain CT and CBCT images) from a first file format into a second file format. In general, both the CT and CBCT images are stored as DICOM format, a standard for handling, storing, printing, and transmitting medical information in hospitals. Information such as the image, imaging modality, and personal data is usually stored in the uncompressed raw data format (e.g., DICOM format) that takes up relatively large storage size and bandwidth during transmission. To facilitate image processing, the CT and CBCT images may be optionally converted from the DICOM format into other commonly used file formats suitable for image processing; for example, TIFF or JPEG format. In one specific embodiment, the CT and CBCT images are respectively converted from DICOM format into TIFF format. Suitable image processing program for converting image data (e.g., from DICOM format into TIFF format) includes, but is not limited to, MATLAB, C, C++, Fortran, and MATHCAD. According to one specific embodiment, the conversion is performed by MATLAB program, a multi-paradigm numerical computing environment and fourth-generation programming language. Typically, MATLAB program makes reference to a computer code that provides a high-level language and interactive environment that enables one to perform computationally intensive tasks.

Still optionally, prior to the step S110, the method 100 may further comprise a step S107 of generating a treatment plan based on the CT images. Accordingly, the clinical practitioners may then administer a treatment (e.g., a radiotherapy) to the subject having or suspected of having a tumor in accordance with the thus-generated treatment plan. Examples of the tumor treatable by the thus generated treatment plan include, but are not limited to, melanoma, leukemia, brain tumor, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, cervical cancer, ovarian cancer, prostate cancer, and head and neck squamous cell carcinoma.

As described in the step S110, the CT and CBCT images are first contoured by use of a contouring model. Suitable contouring models that may be employed in the method 100 include, but are not limited to, circular model, rectangular model, and customized model. In the circular and rectangular models, the images are respectively contoured by circular and rectangular borders, both models employ fixed and unchangeable structures lacking flexibility of adjustment. In contrast, the customized model provides a means for constructing the contour manually, so that the contour may be adjusted and varied to specifically match the shape of the target object. According to one preferred embodiment of the present disclosure, the CT and CBCT images are respectively contoured by the customized model.

Next, in the step S120, the contoured CT and CBCT images are respectively extracted and thereby generate the extracted CT images and the extracted CBCT images. The extraction may be executed by any method familiar with one skilled artisan, for example, the Snake algorithm or the live wire algorithm. According to one working example of the present disclosure, the contoured CT and CBCT images are respectively extracted by the Snake algorithm. Snake, also known as active contour model, is an algorithm used to delineate or extract a target object outline from a 2D image. The algorithm is an energy minimizing, deformable spline influenced by constraint and image forces that pull it towards object contours and internal forces that resist deformation. It has been widely used in applications like object tracking, shape recognition, segmentation, edge detection and stereo matching.

According to certain embodiments, the Snakes algorithm used in the method 100 is expressed as equation (i), $$F_1(C) + F_2(C) = \int_{inside(C)} |u_0 - c_1|^2 dx + \int_{outside(C)} |u_0 - c_2|^2 dx, \quad (i)$$

in which C is the contoured image (i.e., the contoured CT image or the contoured CBCT image), $C_1$ is the average value of pixel intensity inside the contoured image, $C_2$ is the average value of pixel intensity outside the contoured image, $\mu_0$ is the original image (i.e., the CT image or the CBCT image), and x is the coordinate of the original image. Accordingly, $F_1$ constrains the contoured image, $F_2$ expands the contoured image, and $F_1$ and $F_2$ would reach the balance when the contoured image is on the boundary of the original image.

Alternatively, the Snakes algorithm employed in the method 100 may be expressed as equation (v), $$F(c_1, c_2, C) = \int_{\Omega_1=\omega} (u_0(x, y) - c_1)^2 dxdy + \int_{\Omega_2=\Omega-\omega} (u_0(x, y) - c_2)^2 dxdy + v|C|, \quad (v)$$

in which C is the contoured image (i.e., the contoured CT image or the contoured CBCT image), $C_1$ is the average value of pixel intensity inside the contoured image, $C_2$ is the average value of pixel intensity outside the contoured image, $\Omega_1$ is the area inside the contoured image, $\Omega_2$ is the area outside the contoured image, $\Omega$ is whole area (i.e., the sum of $\Omega_1$ and $\Omega_2$), $\omega$ is the pixels set of the area inside the contoured image, $\mu_0$ is the original image (i.e., the CT image or the CBCT image), and x and y are the coordinates of the original image.

In the step S130, the extracted CT and CBCT images are processed to minimize any image dislocation therebetween, which might be derived during scanning. To this purpose, a 3D CT model and a 3D CBCT model are respectively constructed based on the extracted CT and CBCT images of the step S120.

Then, the orientation and dimension of the 3D CBCT model are matched to that of the 3D CT model so that a registered 3D CBCT model is produced as illustrated in the step S140. According to one embodiment of the present disclosure, the 3D CBCT model is matched by iterative closest point (ICP) algorithm, which iteratively computes the parameters of the 3D CT model and the 3D CBCT model so as to adjust the orientation and dimension of the 3D CBCT model. Technically, ICP is an algorithm for minimizing the differences between two clouds of points, and is often used to construct 2D or 3D surface from different scans. Point cloud is a set of digitized data points defining an object in 2D or 3D. In the algorithm, one point cloud, designated as reference or target (i.e., the 3D CT model in the present method), is kept fixed, while the other one (i.e., the 3D CBCT model in the present method), designated as source, is transformed to closely match the reference. The algorithm iteratively revises the transformation via translation, rotation, or the combination thereof, so as to minimize the distance between the source and the reference point clouds.

According to some embodiments of the present disclosure, the ICP algorithm used to match the present 3D CBCT model is expressed as equation (ii), $$E = \sum_{i=1}^{N} |(\vec{p_i'} - \vec{p_i}) - [R(\vec{q_i'} - \vec{q_i}) + T]|, \quad (ii)$$

in which $\vec{p}$ is the grid origin coordinate of the 3D CBCT model, $\vec{p_i}$ is the number i point of the 3D CBCT model, $\vec{p_i'}$ is $\vec{p_i} - \vec{p}$, $\vec{q}$ is the grid origin coordinate of the 3D CT model, $\vec{q_i}$ is the number i point of the 3D CBCT model, $\vec{q_i'}$ is $\vec{q_i} - \vec{q}$, T is a translation vector, and R is a rotation matrix to minimize the value of error E.

Proceeding to the step S150, a plurality of transverse CT and CBCT images are respectively generated from the 3D CT model of the step S130 and the registered 3D CBCT model of the step S140. According to certain embodiments of the present disclosure, the plurality of transverse CT and CBCT images are generated by segmenting the 3D CT model and the registered 3D CBCT model with parallel planes.

In the step S160, the plurality of transverse CT and CBCT images obtained in the step S150 are respectively evaluated by the square difference matching method so as to select the best matching images. According to some embodiments, the matching is determined by the squared difference, in which a lower score represents a better match than that of a high score. According to one embodiment of the present disclosure, the square difference matching method is defined by equation (iii), $$\sum_{x',y'} [I(x', y') - I(x - x', y - y')]^2, \quad (iii)$$

in which x and y are the coordinates of the transverse CT image, x' and y' are the coordinates of the transverse CBCT image, and I is a number to minimize the value of equation (iii). Based on the evaluation result, a target transverse CT image and a target transverse CBCT image respectively having the lowest score (i.e., the highest matched images) are selected.

Finally, in the step S170, the target transverse CT image and the target transverse CBCT image selected in the step S160 are registered to produce the registered image. According to some embodiments of the present disclosure, the registration is exerted by Deformable image registration (DIR). DIR is a technique for modifying a deformable image in an elastic way to match similar features in a reference image. The technique, in general, involves determining a transformation necessary to register (e.g., to align) two images by matching structures of interest in the deformable image with structures of interest within the reference image. The matching process includes deforming the deformable image to achieve alignment of these structures within the two images. According to certain embodiments of the present disclosure, the DIR algorithm executed in the method 100 is based on the original demons algorithm, in which two images Im(x) and Is(x) are registered, and a vector field v(x) relates these two images by Im(x+v(x))=Is(x). Specifically, for Im to be gradually deformed to match Is, Im is termed as the moving image (i.e., the target transverse CT image in the present invention), while Is is called the static image (i.e., the target transverse CBCT image in the present invention). The vector field v(x) is solved in an iterative fashion and at each iteration the increment of the vector field dr(x) is determined based on the image intensity at the voxel x.

In some embodiments of the present disclosure, the present DIR algorithm used to register the target transverse CT image and the target transverse CBCT image comprises three steps. First, the increment of the moving vector (or the displacement vector) at all voxel points is calculated by equation (iv), $$dr^{(k+1)} = \frac{(I_m^{(k)} - I_s)\nabla I_s}{\left(I_m^{(k)} - I_s\right)^2 + |\nabla I_s|^2} + \frac{(I_m^{(k)} - I_s)\nabla I_m^{(k)}}{\left(I_m^{(k)} - I_s\right)^2 + |\nabla I_m^{(k)}|^2}, \quad \text{(iv)}$$

in which dr=(dx,dy,dz) is the voxels of two images (i.e., the target transverse CT image and the target transverse CBCT image), the superscript indexes the iteration step, $I_m^{(k)}$ is the intensity of the target transverse CT image at the kth iteration, Is is the target transverse CBCT image. Then, the resulting incremental vector field dr is smoothed by being convolved with a Gaussian kernel. Third, the incremental deformation field is added to the global deformation field v(x) followed by updating the moving image (i.e., the target transverse CT image). The three steps are iteratively performed until convergence is reached.

According to embodiments of the present disclosure, the registered image produced by the method 100 simultaneously comprises the structural information of CT image (e.g., the CT image with treatment plan, also known as the planning CT image) and CBCT image.

II. System for Registering an Image from CT Images and CBCT Images

The second aspect of the present disclosure pertains to a system 200, which is configured to perform the method 100 provided in Section I. The system 200 comprises, a user interface 210, which is configured to receive an input of commands from a user and provide an output to the user; and a processing unit 230, which is controlled by the user interface 210 and is configured to perform the method 100. More specifically, the processing unit 230 is configured to, (a) respectively contour the plurality of CT images and the plurality of CBCT images to create a plurality of contoured CT images and a plurality of contoured CBCT images;

(b) respectively extract the plurality of contoured CT images and the plurality of contoured CBCT images of the step (a) to create a plurality of extracted CT images and a plurality of extracted CBCT images;

(c) respectively construct a 3D CT model and a 3D CBCT model from the plurality of extracted CT images and the plurality of extracted CBCT images of the step (b);

(d) create a registered 3D CBCT model by matching the 3D CBCT model to the 3D CT model of the step (c);

(e) respectively generate a plurality of transverse CT images and a plurality of transverse CBCT images from the 3D CT model of the step (c) and the registered 3D CBCT model of the step (d);

(f) respectively select one target transverse CT image and one target transverse CBCT image from the plurality of transverse CT images and the plurality of transverse CBCT images of the step (e); and (g) register the respectively selected target transverse CT image and CBCT image of the step (f) to create the registered image.

The steps (a)-(g) performed by the processing unit 230 are quite similar to the method 100 as described above, and hence, detailed description thereof is omitted herein for the sake of brevity.

Further, as described in the method 100 of Section I, to facilitate the image processing, the processing unit 230 may be further configured to convert each of the plurality of CT and CBCT images from a first file format into a second file format. According to some embodiments, the first format is DICOM format, and the second format is TIFF or JPEG format. According to one embodiment, the image conversion is performed by MATLAB program.

Optionally, the system 200 may further comprise a communication port 250 that is coupled to the user interface 210. Thus, the CT and CBCT images may be imported into the system 200 and/or exported as the registered images through the communication port 250, which, for example, may be any of a serial port, a universal serial bus (USB) port, or a micro-USB port.

Still optionally, the system 200 may further comprise a storage unit, which is configured to store the imported image (i.e., the CT or CBCT image) and the registered image.

In one embodiment of the present disclosure, the system 200 further comprises a display, which is operably connected to the user interface 210 and is configured to display the imported image (i.e., the CT or CBCT image) and the registered image.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

In the present disclosure, 242 planning CT images (i.e., the CT images with the information of treatment plan) and 140 CBCT images were collected from MacKay Memorial Hospital, Taipei, Taiwan, R.O.C. The collected planning CT and CBCT images were processed by the following steps in sequence to generate a registered image suitable for medical applications, for example, radiotherapy.

Step 1. Converting the Images by MATLAB Program

To generate the registered image, the planning CT image and the corresponding CBCT image were respectively converted from DICOM format into TIFF format by MATLAB program.

Step 2. Extracting the Images by Snake Algorithm

The converted planning CT and CBCT images were then contoured by circular model, rectangular model, or customized model. Compared to the results respectively obtained from the circular model and rectangular model, the shape of the contoured image generated by the customized model fitted well with the converted images (data not shown).

Next, the contoured CT and CBCT images were extracted by Snake algorithm, which was expressed as equation (i), $$F_1(C) + F_2(C) = \int_{inside(C)} |u_0 - c_1|^2 dx + \int_{outside(C)} |u_0 - c_2|^2 dx, \quad \text{(i)}$$

in equation (i), C is the contoured image (i.e., the contoured CT image or the contoured CBCT image), $C_1$ is the average value of pixel intensity inside the contoured image, $C_2$ is the average value of pixel intensity outside the contoured image, $\mu_0$ is the original image (i.e., the planning CT image or the CBCT image), and x is the coordinate of the original image. In the algorithm, $F_1$ constrained the contoured image, $F_2$ expanded the contoured image, and $F_1$ and $F_2$ eventually reach the balance when the contoured image is on the boundary of the original image.

The results indicated that when $F_1(C)>0$ and $F_2(C)\approx 0$, the contoured image was outside the original image; when $F_1(C)\approx 0$ and $F_2(C)>0$, the contoured was inside the original image; when $F_1(C)>0$ and $F_2(C)>0$, the contoured image was partially inside the original image; and when $F_1(C)\approx 0$ and $F_2(C)\approx 0$, the fitting energy would be minimized, and the contoured image would superimpose nicely with the original image (data not shown). Thus, the extracted image may be larger, smaller or equal to the original image depending on the parameter set in the Snake algorithm.

Figure 3:
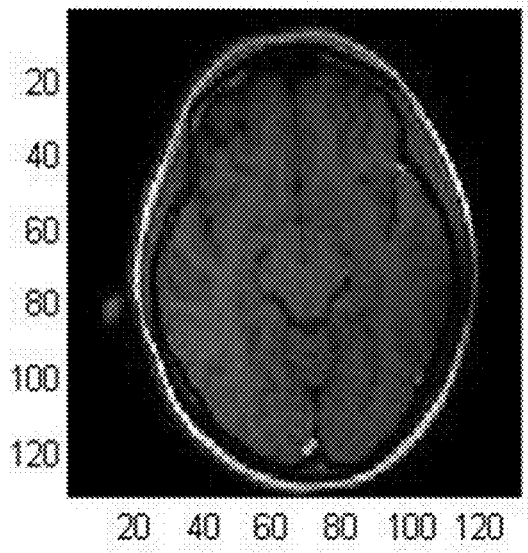
FIG. 3 depicts the CT image (Panel (A)) and the Snake-extracted image (Panel (B)) according to one example of the present disclosure.
Figure 3:
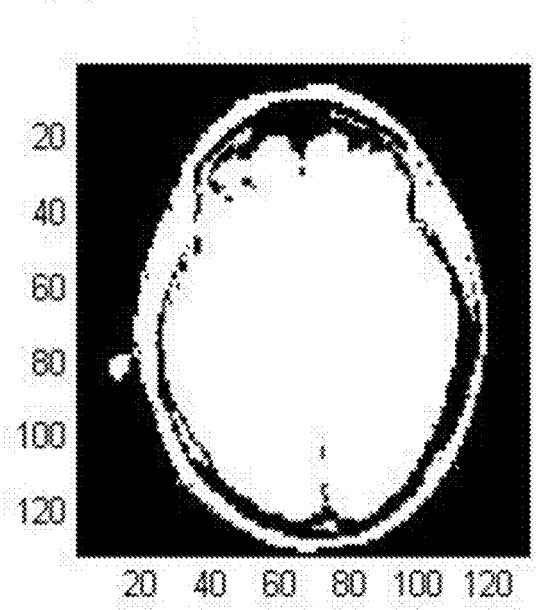
Figure 4:
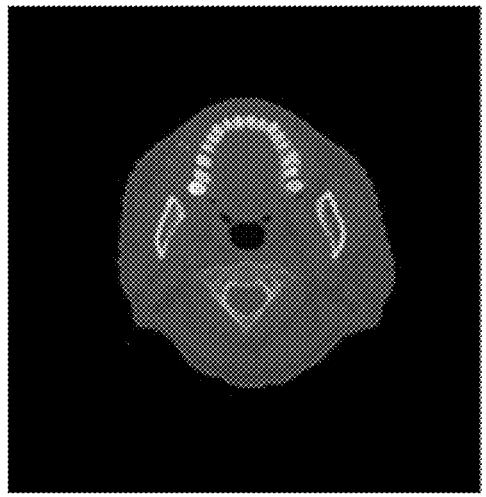
FIG. 4 depicts the CT image (Panel (A)) and the CBCT image (Panel (B)) extracted by Snakes algorithm according to one example of the present disclosure.
Figure 4:

FIG. 3 depicted the CT images before (Panel (A)) and after (Panel (B)) the extraction performed by Snake algorithm, respectively. According to the data of FIG. 4, both the CT image (Panel (A)) and the CBCT image (Panel (B)) can be successfully extracted by the present Snake algorithm.

Step 3. Matching the Images by ICP Algorithm

Figure 5:
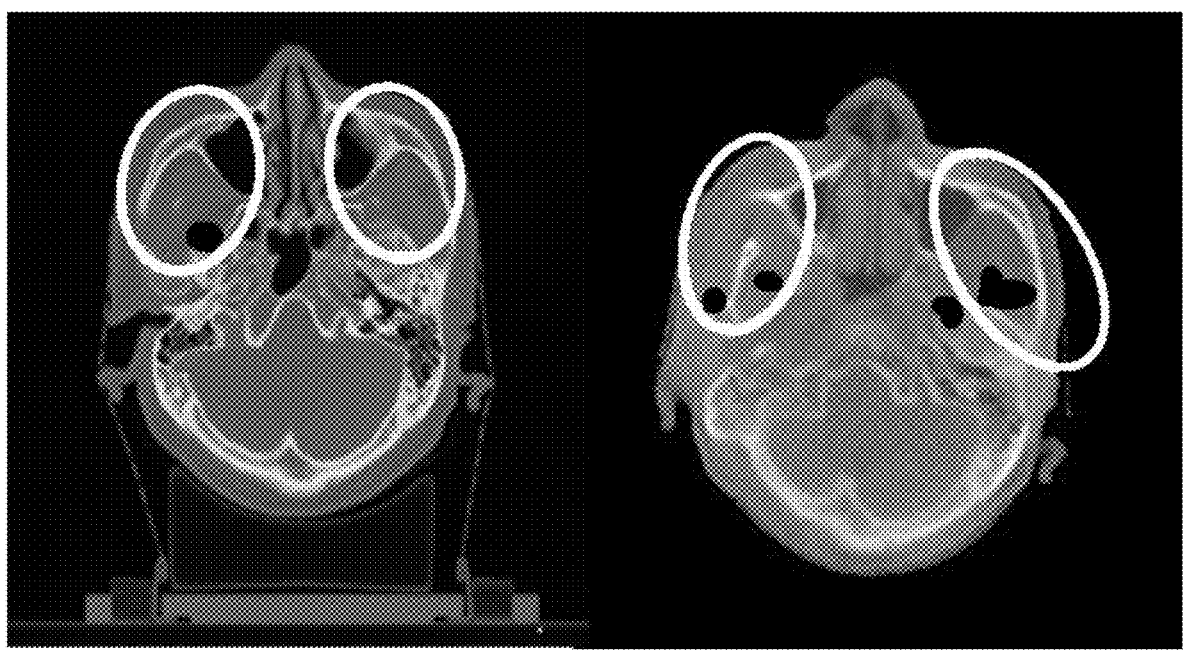
FIG. 5 are photographs respectively derived from CT scan (left image) and CBCT scan (right image) that depict the dislocations (indicated by the borders) between the two images according to one example of the present disclosure.

FIG. 5 depicted the image dislocations that usually occurred during the CT and CTCB scanning, in which the dislocations on the CT image (FIG. 5, left image) and the CBCT image (FIG. 5, right image) were circled.

Figure 6:
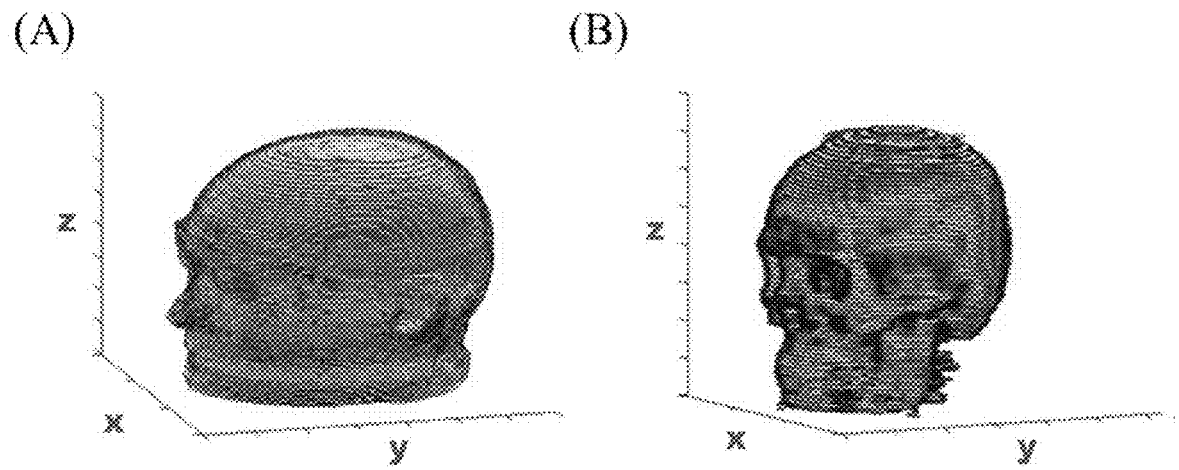
FIG. 6 are representative images of 3D models respectively constructed from extracted CT and CBCT images according to another example of the present disclosure, in which the 3D model of the extracted CT image was depicted in Panel (A), and the 3D model of the extracted CBCT image was depicted in Panel (B)

To calibrate the dislocations, the 3D CT model (FIG. 6, Panel (A)) and the 3D CBCT model (FIG. 6, Panel (B)) were respectively constructed using the extracted CT and CBCT images generated in the Step 2. Then, the 3D CBCT model was matched to 3D CT model by use of the ICP algorithm as the shown in equation (ii), in which $\vec{p}$ is the grid origin coordinate of the 3D CBCT model, $\vec{p_i}$ is the number i point of the 3D CBCT model, $\vec{p}$ is $\vec{p_i} - \vec{p_i'}$, $\vec{p}$ is the grid origin coordinate of the 3D CT model, $\vec{q_i}$ is the number i point of the 3D CBCT model, $\vec{q_i'}$ is $\vec{q_i} - \vec{q}$, T is a translation vector, and R is a rotation matrix to minimize the value of error E;

$$E = \sum_{i=1}^{N} |(\vec{p_i'} - \vec{p_i}) - [R(\vec{q_i'} - \vec{q_i}) + T]|, \qquad (ii)$$

In the algorithm, the 3D CT model was set as the reference and was kept fixed, while the 3D CBCT model was set as the source that was transformed to closely match the reference.

Step 4. Selecting the Most Similar Images

Respectively segmenting the 3D CT model and the matched CBCT model of the Step 3 to generate transverse CT and CBCT images, where a target transverse CT image and a target transverse CBCT image were selected by use of the square difference matching method to obtain the best matched images; the square difference matching method was expressed as the equation (iii), $$\Sigma_{x',y'}[(x',y')-I(x-y',y-y')]^2 \qquad (iii),$$

in which x and y are the coordinates of the transverse CT image, x' and y' are the coordinates of the transverse CBCT image, and I is a number to minimize the value of the equation.

Step 5. Registering the Best Matched Images

The target transverse CT image and the target transverse CBCT image selected in the Step 4 were then registered by use of DIR algorithm. First, the increment of the moving vector (or the displacement vector) at all voxel points was calculated by equation (iv), $$dr^{(k+1)} = \frac{(I_m^{(k)} - I_s)\nabla I_s}{(I_m^{(k)} - I_s)^2 + |\nabla I_s|^2} + \frac{(I_m^{(k)} - I_s)\nabla I_m^{(k)}}{(I_m^{(k)} - I_s)^2 + |\nabla I_m^{(k)}|^2}, \qquad (iv)$$

in which dr=(dx,dy, dz) is the voxels of target transverse CT image and target transverse CBCT image, the superscript indexes the iteration step, $I_m^{(k)}$ is the intensity of the target transverse CT image at the kth iteration, Is is the target transverse CBCT image. Then, the resulting incremental vector field dr was smoothed by being convolved with a Gaussian kernel. Finally, the incremental deformation field was added to the global deformation field v(x) followed by updating the target transverse CT image. The three steps were iteratively performed until convergence was reached.

Figure 7:
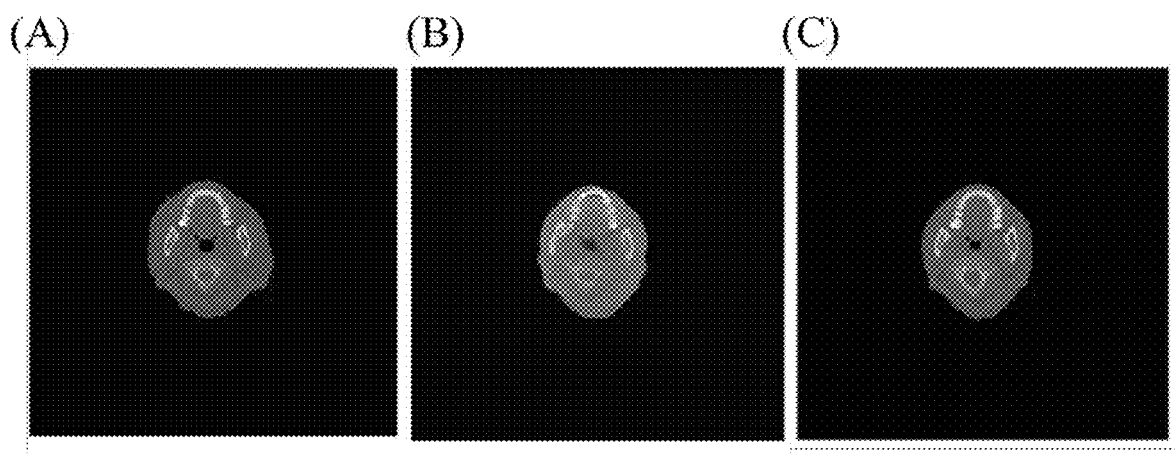
FIG. 7 are representative photographs that respectively depict the CT image (Panel (A)), CBCT image (Panel (B)), and registered image (Panel (C)) according to one example of the present disclosure.

FIG. 7 depicted the images before and after registration, in which the CT and CBCT images before registration were respectively depicted in Panels (A) and (B) of FIG. 7, and the registered image generated by the present method was depicted in Panel (C) of FIG. 7.

In conclusion, the present disclosure provides a system and a method for registering an image that integrates the information of CT and CBCT images. The present system and method may be applied to the field of radiotherapy, and accordingly, provide a potential means to improve the efficacy of tumor treatment.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A computer implemented method for creating a registered image from a plurality of computed tomography (CT) images and a plurality of cone-beam computed tomography (CBCT) images, comprising,
   (a) respectively contouring the plurality of CT images and the plurality of CBCT images to create a plurality of contoured CT images and a plurality of contoured CBCT images;
   (b) respectively extracting the plurality of contoured CT images and the plurality of contoured CBCT images of the step (a) to create a plurality of extracted CT images and a plurality of extracted CBCT images;
   (c) respectively constructing a three dimensional (3D) CT model and a 3D CBCT model from the plurality of extracted CT images and the plurality of extracted CBCT images of the step (b);
   (d) creating a registered 3D CBCT model by matching the 3D CBCT model to the 3D CT model of the step (c);
   (e) respectively generating a plurality of transverse CT images and a plurality of transverse CBCT images from the 3D CT model of the step (c) and the registered 3D CBCT model of the step (d);

(f) respectively selecting one target transverse CT image and one target transverse CBCT image from the plurality of transverse CT images and the plurality of transverse CBCT images of the step (e); and (g) registering the respectively selected target transverse CT image and CBCT image of the step (f) to create the registered image.

2. The computer implemented method of claim 1, wherein in the step (b), the plurality of contoured CT images and the plurality of contoured CBCT images are respectively extracted by equation (i), $$F_1(C) + F_2(C) = \int_{inside(C)} |u_0 - c_1|^2 dx + \int_{outside(C)} |u_0 - c_2|^2 dx, \quad (i)$$

wherein, in the creation of each of the plurality of extracted CT images, C is the contoured CT image, $C_1$ is the average value of pixel intensity inside the contoured CT image, $C_2$ is the average value of pixel intensity outside the contoured CT image, $\mu_0$ is the CT image; and x is the coordinate of the CT image; and in the creation of each of the plurality of extracted CBCT images, C is the contoured CBCT image, $C_1$ is the average value of pixel intensity inside the contoured CBCT image, $C_2$ is the average value of pixel intensity outside the contoured CBCT image, $\mu_0$ is the CBCT image; and x is the coordinate of the CBCT image.

3. The computer implemented method of claim 1, wherein in the step (d), the registered 3D CBCT model is created by equation (ii), $$E = \sum_{i=1}^{N} |(\vec{p_i'} - \overline{p_i}) - [R(\vec{q_i'} - \overline{q_i}) + T]|, \quad (ii)$$

wherein, $\vec{p}$ is the grid origin coordinate of the 3D CBCT model, $\overline{p_i}$ is the number i point of the 3D CBCT model, $\vec{p_i'}$ is $\vec{p} - \overline{p_i}$, $\vec{q_i}$ is the grid origin coordinate of the 3D CT model, $\overline{q_i}$ is the number i point of the 3D CBCT model, $\vec{q_i'}$ is $\overline{q_i} - \vec{q}$, T is a translation vector, and R is a rotation matrix to minimize the value of error E.

4. The computer implemented method of claim 1, wherein in the step (f), the target transverse CT image and the target transverse CBCT image are selected by equation (iii), $$\sum_{x',y'} [(x', y') - I(x - x', y - y')]^2, \quad (iii)$$

wherein, x and y are the coordinates of each of the plurality of transverse CT image, x' and y' are the coordinates of each of the plurality of transverse CBCT image, and I is a number to minimize the value of equation (iii).

5. The computer implemented method of claim 1, wherein in the step (g), the respectively selected target transverse CT image and CBCT image of step (f) are registered by equation (iv), $$dr^{(k+1)} = \frac{(I_m^{(k)} - I_s)\nabla I_s}{(I_m^{(k)} - I_s)^2 + |\nabla I_s|^2} + \frac{(I_m^{(k)} - I_s)\nabla I_m^{(k)}}{(I_m^{(k)} - I_s)^2 + |\nabla I_m^{(k)}|^2}, \quad (iv)$$

wherein, dr is the voxels of the target transverse CT image and the target transverse CBCT image, $I_m^{(k)}$ is the intensity of the target transverse CT image at the kth iteration, and Is is the target transverse CBCT image.

6. The computer implemented method of claim 1, further comprising respectively converting the plurality of CT images and the plurality of CBCT images from a first file format into a second file format prior to the step (a).

7. The computer implemented method of claim 6, wherein the first file format is digital imaging and communications in medicine (DICOM) format; and
the second file format is tagged image file format (TIFF) or joint photographic expert group (JPEG) format.

8. The computer implemented method of claim 1, further comprising generating a treatment plan on the plurality of CT images prior to the step (a).

9. A system for creating a registered image from a plurality of CT images and a plurality of CBCT images, comprising,
a user interface configured to receive an input of commands from a user and provide an output to the user; and
a processing unit that is controlled by the user interface and is configured to execute the computer implemented method of claim 1.

10. The system of claim 9, further comprising a communication port coupled to the user interface.

11. The system of claim 10, wherein the communication port is any of a serial port, a universal serial bus (USB) port, or a micro-USB port.

12. The system of claim 9, wherein the processing unit is further configured to respectively convert the plurality of CT images and the plurality of CBCT images from a first file format into a second file format.

13. The system of claim 12, wherein
the first file format is DICOM, and
the second file format is TIFF or JPEG.

14. A method of treating a cancer in the subject, comprising:
(a) obtaining a plurality of CT images and a plurality of CBCT images of the subject;
(b) generating a treatment plan on the plurality of CT images of the step (a);
(c) creating a registered image with the treatment plan from the plurality of CT images of the step (b) and the plurality of CBCT images of the step (a) by the computer implemented method of claim 1; and
(d) administering to the subject a treatment in accordance with the registered image of the step (c).

15. The method of claim 14, wherein the treatment is a radiotherapy.

16. The method of claim 14, wherein the cancer is a melanoma, leukemia, brain tumor, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, cervical cancer, ovarian cancer, prostate cancer, or head and neck squamous cell carcinoma.

17. The method of claim 14, wherein the subject is a human.

* * * * *